US00PP19029P2

(12) United States Plant Patent
Ren

(10) Patent No.: US PP19,029 P2
(45) Date of Patent: Jul. 15, 2008

(54) *CALIBRACHOA* PLANT NAMED 'BALCABPEA'

(50) Latin Name: *Calibrachoa×hybrida*
Varietal Denomination: Balcabpea

(75) Inventor: Jianping Ren, Geneva, IL (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 11/823,391

(22) Filed: Jun. 27, 2007

(51) Int. Cl.
*A01H 5/00* (2006.01)

(52) U.S. Cl. ..... Plt./413

(58) Field of Classification Search ..... Plt./413
See application file for complete search history.

(56) References Cited

U.S. PATENT DOCUMENTS

PP14,172 P2 * 9/2003 Klemm ..... Plt./413

OTHER PUBLICATIONS

Canada Plant Breeders' Rights application No. 07–5858 filed Apr. 12, 2007—not published when this IDS was prepared.

* cited by examiner

*Primary Examiner*—Wendy C. Haas
(74) *Attorney, Agent, or Firm*—Audrey Charles

(57) ABSTRACT

A new and distinct cultivar of *Calibrachoa* plant named 'Balcabpea', characterized by its single type pink-colored flowers with distinct venation, medium green-colored foliage, and moderately vigorous, mounded-trailing growth habit.

1 Drawing Sheet

Latin name of genus and species of plant claimed: *Calibrachoa×hybrida.*
Variety denomination: 'Balcabpea'.

BACKGROUND OF THE INVENTION

The present invention relates to a new and distinct cultivar of *Calibrachoa* plant botanically known as *Calibrachoa×hybrida* and hereinafter referred to by the cultivar name 'Balcabpea'.

The new cultivar originated in a controlled breeding program in Elburn, Ill. during October 2004. The objective of the breeding program was the development of *Calibrachoa* cultivars with attractive flower coloration, medium green-colored foliage, and a moderately vigorous, mounded-trailing growth habit.

The new *Calibrachoa* cultivar is the result of cross-pollination. The female (seed) parent of the new cultivar is the proprietary *Calibrachoa×hybrida* breeding selection designated 2155-1B, not patented, characterized by its single type light pink-colored flowers lacking distinct venation color, medium green-colored foliage, and mounded and trailing growth habit. The male (pollen) parent of the new cultivar is the proprietary *Calibrachoa×hybrida* breeding selection designated 2170-7B, not patented, characterized by its single type bright salmon-colored flowers, medium green-colored foliage, and prostrate growth habit. The new cultivar was discovered and selected as a single flowering plant within the progeny of the above stated cross-pollination during August 2005 in a controlled environment at Elburn, Ill.

Asexual reproduction of the new cultivar by terminal stem cuttings since August 2005 at Elburn, Ill. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balcabpea' as a new and distinct cultivar of *Calibrachoa* plant:

1. Single type, pink-colored flowers with distinct venation;
2. Medium green-colored foliage; and
3. Moderately vigorous, mounded-trailing growth habit.

Plants of the new cultivar differ from plants of the female parent primarily in venation color of the flower and from plants of the male parent primarily in flower color and growth habit.

Of the many commercially available *Calibrachoa* cultivars known to the inventor, the most similar in comparison to the new cultivar is MiniFamous™ Apricot Dream 'KLEC01061', U.S. Plant Pat. No. 14,172. However, in side by side comparisons, plants of the new cultivar differ from plants of 'KLEC01061' in the following characteristics:

1. Plants of the new cultivar have a flower color different from plants of 'KLEC01061'; and
2. Plants of the new cultivar have a mature stem color different from plants of 'KLEC01061'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balcabpea'. The plants were grown in 4.5 inch pots for 6 weeks in a greenhouse at West Chicago, Ill. Plants were given one pinch at transplant.

DETAILED BOTANICAL DESCRIPTION

Figure 1:
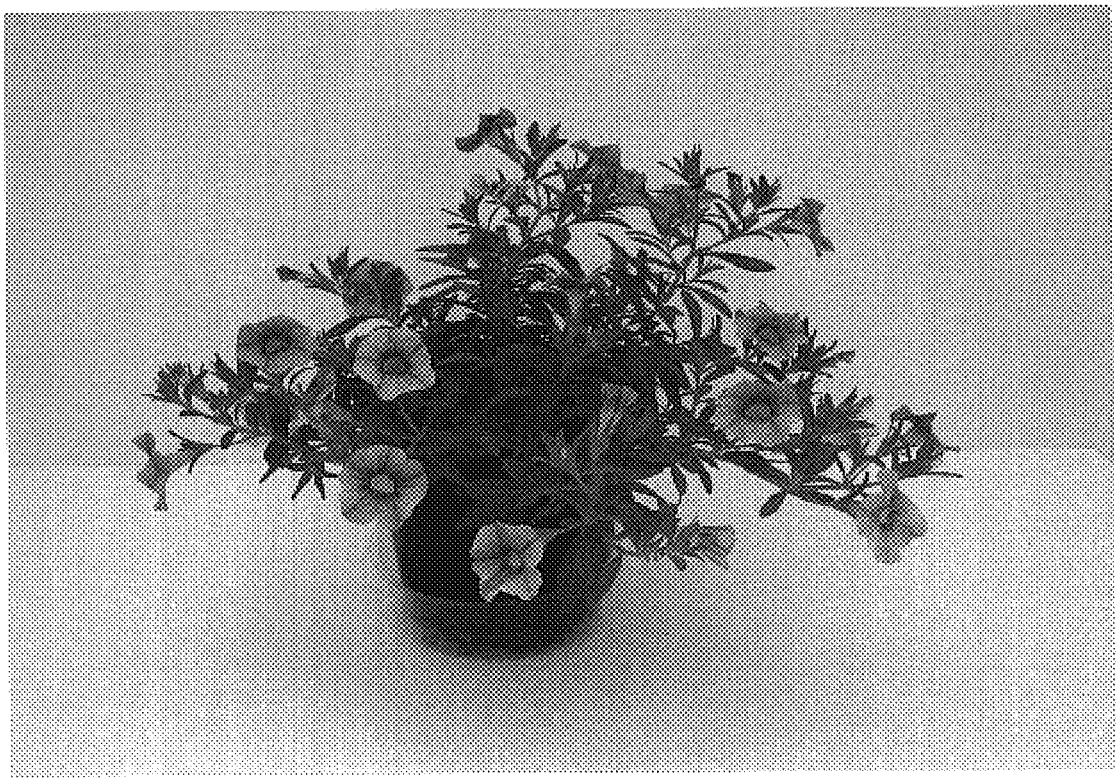
FIG. 1 illustrates a side view of the overall growth and flowering habit of 'Balcabpea'.
Figure 2:
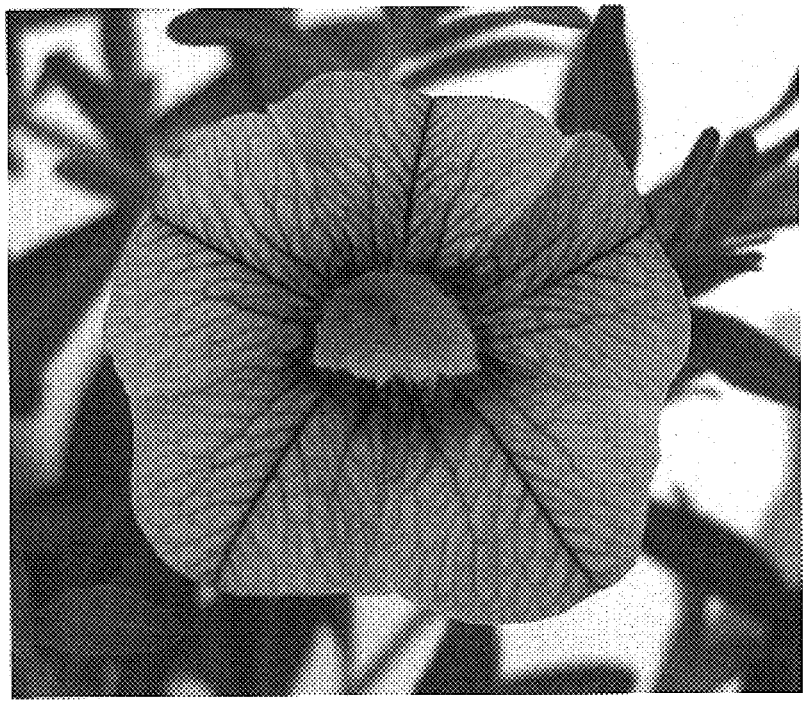
FIG. 2 illustrates a close-up view of an individual flower of 'Balcabpea'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on May 2, 2007 between 9:00 a.m. and 11:00 a.m. under natural light conditions in West Chicago, Ill.

The following descriptions and measurements describe plants produced from cuttings taken from stock plants and grown in a glass-covered greenhouse under conditions comparable to those used in commercial practice. The plants were grown at West Chicago, Ill. in 4.5 inch pots for 6 weeks utilizing a soilless growth medium. Plants were given one pinch at transplant. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day.

Botanical classification: *Calibrachoa×hybrida* cultivar Balcabpea.

Parentage:

*Female parent.*—Proprietary *Calibrachoa×hybrida* breeding selection designated 2155-1B, not patented.

*Male parent.*—Proprietary *Calibrachoa×hybrida* breeding selection designated 2170-7B, not patented.

Propagation:

*Type cutting.*—Terminal stem.

*Time to initiate roots.*—Approximately 6 to 8 days.

*Time to produce a rooted cutting.*—Approximately 24 to 28 days.

*Root description.*—Fibrous.

*Rooting habit.*—Freely branching.

Plant description:

*Commercial crop time.*—Approximately 6 to 7 weeks from a rooted cutting to finish in a 10 cm pot.

*Growth habit and general appearance.*—Moderately vigorous, mounded-trailing growth habit.

*Size.*—Height from soil level to top of plant plane: Approximately 9.6 cm. Width: Approximately 25.7 cm.

*Branching habit.*—Freely branching, pinching improves basal branching. Quantity of main branches per plant: Approximately 6.

*Branch.*—Strength: Moderate. Length: Approximately 14.0 cm. Diameter: Approximately 2.0 mm. Length of central internode: Approximately 1.2 cm. Texture: Densely glandular pubescent. Gland color: Colorless, transparent. Color of young stem: 144B. Color of mature stem: 144A.

Foliage description:

*General description.*—Quantity of leaves per main branch: Approximately 20. Fragrance: Slight. Form: Simple. Arrangement on flowering stem: Opposite.

*Leaves.*—Aspect: At acute angle to stem with tip turning downward. Shape: Elliptic. Margin: Entire. Apex: Acute. Base: Attenuate. Venation pattern: Pinnate. Length of mature leaf: Approximately 3.5 cm. Width of mature leaf: Approximately 1.1 cm. Texture of upper surface: Densely glandular pubescent. Texture of lower surface: Sparsely glandular pubescent, dense on venation. Gland color: Colorless, transparent. Color of upper surface of young foliage: 137A with venation of 144C. Color of lower surface of young and mature foliage: 138B with venation of 138C. Color of upper surface of mature foliage: 137B with venation of 144C.

*Petiole.*—Length: Approximately 2.8 mm. Diameter: Approximately 1.0 mm. Texture: Densely glandular pubescent. Gland color: Colorless, transparent: Color: 144C.

Flowering description:

*Flowering habit.*—'Balcabpea' is freely flowering under outdoor growing conditions with substantially continuous blooming from spring through autumn and year-round in greenhouse environment.

*Lastingness of individual flower on the plant.*—Approximately 9 to 11 days.

Flower description:

*General description.*—Type: Single, salverform. Quantity per plant: Approximately 20. Fragrance: None.

*Bud.*—Rate of opening: Generally takes 3 to 4 days for bud to progress from first color to fully open flower. Quantity per plant: Approximately 6.2.

*Bud just before opening.*—Shape: Oblong. Length: Approximately 2.2 cm. Diameter: Approximately 6.0 mm. Texture: Densely glandular pubescent. Gland color: Colorless, transparent. Color: Petals of 54C and venation of 187D darkening on midveins to 187A; corolla tube of 1C with venation of 1B.

*Corolla.*—Diameter: Approximately 3.3 cm.

*Petals.*—Quantity: 5, fused to form a tube. Shape: Obovate. Margin: Entire. Apex: Obtuse, some acuminate. Length from tube: Approximately 1.4 cm. Length of free portion: Approximately 5.3 mm. Width: Approximately 1.6 cm. Texture of upper surface: Glabrous. Texture of lower surface: Densely glandular pubescent. Gland color: Colorless, transparent. Color of upper surface when first open: N66D with N66B at throat opening and venation of 187D darkening on midveins to 187A. Color of lower surface when first and fully open: 65C with venation of 187D darkening on midveins to 187A. Color of upper surface when fully open: N66D with N66B at throat opening and venation of 187D darkening on midveins to 187A; background fades to 38B with age.

*Corolla tube.*—Length: Approximately 1.9 cm. Diameter at distal end: Approximately 8.2 mm. Diameter at proximal end: Approximately 1.0 mm. Texture of inner surface: Glabrous. Texture of outer surface: Glandular pubescent. Gland color: Colorless, transparent. Color of inner surface: 12A with venation of 1B. Color of outer surface: 1C with venation of 1B.

*Peduncle.*—Strength: Strong. Aspect: Acute angle to stem. Length: Approximately 2.2 cm. Diameter: Approximately 1.0 mm. Texture: Densely glandular pubescent. Gland color: Colorless, transparent. Color: 144B.

*Sepals.*—Quantity per flower: 5, fused along lower half. Shape: Lanceolate. Apex: Acute. Length: Approximately 1.6 cm. Width: Approximately 3.0 mm. Texture of upper and lower surfaces: Densely glandular pubescent. Gland color: Colorless, transparent. Color of upper surface: 137A. Color of lower surface: 137C with 144C at base.

*Reproductive organs.*—Androecium: Stamen quantity: 5 per flower, basifixed. Stamen length: Approximately 1.1 cm. Filament length of free portion: Approximately 6.0 mm. Filament color: 154D. Anther shape: 2 parted, oval. Anther length: Less than 1 mm. Anther color: 8A. Pollen amount: Abundant. Pollen color: 8B. Gynoecium: Pistil quantity: 1 per flower. Pistil length: Approximately 1.2 cm. Stigma shape: Funnel. Stigma length: Less than 1 mm. Stigma color: 144A. Style length: Approximately 1.0 cm. Style color: 144B. Ovary diameter: Approximately 2.0 mm. Ovary color: N144C.

Seed and fruit production: Neither seed nor fruit production has been observed.

Disease and pest resistance: Resistance to pathogens and pests common to *Calibrachoa* has not been observed.

What is claimed is:

1. A new and distinct cultivar of *Calibrachoa* plant named 'Balcabpea', substantially as herein shown and described.

* * * * *